(12) United States Patent
Smith et al.

(10) Patent No.: US 12,076,450 B2
(45) Date of Patent: *Sep. 3, 2024

(54) AIR HANDLING SYSTEM FOR HOT AIR STERILIZER

(71) Applicant: Integrated Medical Technologies, Inc., Bloomington, IL (US)

(72) Inventors: William Bryan Smith, Bloomington, IL (US); Michael Howard Linse, Corvallis, OR (US); Nelson Sigman Slavik, Niles, MI (US); Gary Jay Oliver, Corvallis, OR (US)

(73) Assignee: Integrated Medical Technologies, Inc., Bloomington, IL (US)

( * ) Notice: Subject to any disclaimer, the term of this patent is extended or adjusted under 35 U.S.C. 154(b) by 82 days.

This patent is subject to a terminal disclaimer.

(21) Appl. No.: 17/882,520

(22) Filed: Aug. 5, 2022

(65) Prior Publication Data

US 2022/0370655 A1 Nov. 24, 2022

Related U.S. Application Data

(63) Continuation of application No. 16/279,091, filed on Feb. 19, 2019, now Pat. No. 11,406,725.
(Continued)

(51) Int. Cl.
*A61L 2/06* (2006.01)
(52) U.S. Cl.
CPC .............. *A61L 2/06* (2013.01); *A61L 2202/14* (2013.01); *A61L 2202/15* (2013.01)

(58) Field of Classification Search
CPC . A61L 2/0023; A61L 2/04; A61L 2/06; A61L 2202/122; A61L 2202/14; A61L 2202/15; A61L 2202/24
See application file for complete search history.

(56) References Cited

U.S. PATENT DOCUMENTS

| 4,935,604 A | 6/1990 | Allen et al. |
| 8,132,870 B2 | 3/2012 | Buczynski et al. |

(Continued)

OTHER PUBLICATIONS

Office Action for U.S. Appl. No. 16/279,091, "Dual-Pass-Through Countertop High Velocity Hot Air Sterilizer", mailed on Mar. 23, 2021, 10 pages.
(Continued)

*Primary Examiner* — Timothy C Cleveland
(74) *Attorney, Agent, or Firm* — Lee & Hayes, P.C.

(57) ABSTRACT

An air handling system for a hot air sterilizer apparatus includes a sterilization chamber having an air exhaust portal, an air handling pathway traversing above the sterilization chamber through an upper supply air plenum and traversing below the sterilization chamber through a lower supply air plenum, a circulation fan configured to direct supply air from the air exhaust portal over an upper heating element through the upper supply air plenum and over a lower heating element through the lower supply air plenum, a first temperature sensor in the upper supply air plenum and configured to measure temperature of air downstream from the upper heating element, a second temperature sensor in the lower supply air plenum and configured to measure temperature of air downstream from the lower heating element, and a third temperature sensor at the air exhaust portal and configured to monitor temperature of air exiting the sterilization chamber.

13 Claims, 8 Drawing Sheets

Related U.S. Application Data

(60) Provisional application No. 62/632,906, filed on Feb. 20, 2018.

(56) References Cited

U.S. PATENT DOCUMENTS

| | | | |
|---|---|---|---|
| 9,463,257 B1 * | 10/2016 | Slavik | A61L 2/06 |
| 10,188,761 B2 | 1/2019 | Tan et al. | |
| 11,406,725 B2 * | 8/2022 | Smith | A61L 2/06 |
| 2017/0175069 A1 | 6/2017 | Baker, Jr. et al. | |

OTHER PUBLICATIONS

Office Action for U.S. Appl. No. 16/279,091, "Dual-Pass-Through Countertop High Velocity Hot Air Sterilizer", mailed on Apr. 15, 2020, 10 pages.

Rogers, W.J., "2-Steam and dry heat sterilization of biomaterials and medical devices", Sterilisation of Biomaterials and Medical Devices, pp. 20-55, 2012, ISBN 9780857096265.20.

Office Action for U.S. Appl. No. 16/279,091, "Dual-Pass-Through Countertop High Velocity Hot Air Sterilizer," mailed on Aug. 18, 2020, 9 pages.

Office Action for U.S. Appl. No. 10/072,021, "Dual-Pass-Through Countertop High Velocity Hot Air Sterilizer," mailed on U.S. Appl. No. 10/072,021, 12 pages.

* cited by examiner

AIR HANDLING SYSTEM FOR HOT AIR STERILIZER

CROSS-REFERENCE TO RELATED APPLICATION

This application is a continuation of U.S. patent application Ser. No. 16/279,091, entitled "DUAL-PASS-THROUGH COUNTERTOP HIGH VELOCITY HOT AIR STERILIZER," filed Feb. 19, 2019, which claims the benefit of U.S. Provisional Patent Application No. 62/632,906, entitled "Double-Door, Pass-Through Countertop High Velocity Hot Air Sterilizer", filed Feb. 20, 2018, the entire disclosures of which are all expressly incorporated herein by reference.

BACKGROUND

There are three distinct types of dry heat sterilizers: (1) Static hot air sterilizers in which air convection is generated solely by gravity as hot air rises and cooler air descends; (2) Mechanical convection sterilizers in which air is moved by blowers to uniformly distribute heated air and equally transfer heat throughout a load; and (3) High velocity hot air sterilizers in which air is moved at various high rates, with flowing air serving as a heat transfer medium. Both static air and mechanical convection sterilizers require minimally one hour (at 340° F.) or two hours (at 320° F.) to achieve sterilization whereas high velocity hot air sterilizer can sterilize in six to twelve minutes (at 375° F.), depending on instrument type or packaging.

A high velocity hot air sterilization device has been disclosed by Cox et al. in U.S. Pat. Nos. 4,824,644; 4,894,207; 4,923,681; and 4,975,245. The single-door high velocity hot air sterilization device of Cox was designed and marketed for use in the dental and orthodontic markets to rapidly sterilize small instruments without instrument corrosion. The device accommodates wrapped or unwrapped instruments which are placed into a wire mesh, open basket and held for a specified time at 375° F. as prescribed under the U.S. FDA 510(k) notification. The basket containing the instruments is placed into the sterilizer through a door located at the front of the sterilizer. Upon completion of the sterilization cycle the basket is removed from the sterilizer though that front door. The air handling system to supply air to and to exhaust air from the sterilization chamber was designed specifically for this small, single-door sterilizer to provide adequate air and temperature distribution within the sterilization chamber for sterilizing small instruments and small instrument loads.

The Cox device supplies high velocity hot air to a sterilization chamber vertically through a plenum located underneath the sterilization chamber. This air supply is pushed through a perforated jet plate to create high velocity streams of air that traverse a short distance to a deflector plate located on a ceiling of the sterilization chamber. The deflector plate redirects the air, causing turbulence required to mix air to a more uniform temperature within the sterilization chamber. As air is supplied to the sterilization chamber there is an equal exhaustion of the chamber air at a rear wall of the sterilization chamber perpendicular to the direction of air entry from under the sterilization chamber. The air exhausts the sterilization chamber by way of a fan wheel, subsequently re-heated, and returned to the air supply plenum underneath the sterilization chamber for the continuous recharging of the sterilization chamber's hot, high velocity air supply. For this system to provide the aerodynamics of rapid airflow required to heat instruments to a temperature that will allow rapid instrument sterilization while providing a narrow range of temperature to avoid material incompatibility of instruments and their packaging, internal dimensions of the sterilization chamber are limited. The sterilization chamber of Cox comprises a width of 10 inches, a depth of 8 inches, and a height of 4 inches. Attempts to increase the sterilization chamber size under the embodiments of Cox resulted in increasing already large temperature ranges generated in the existing sterilization chamber and resulted in inconsistent and inadequate microbial kill efficacies across all three dimensions of the sterilization chamber.

While effective for instrument sizes and load capacities found in dental and orthodontic practices, the air handling system of the Cox device is limited in application and capability to serve the expanded requirements and needs of a healthcare facility such as a hospital or clinic. To service instrument processing needs in a healthcare environment a sterilizer must have a capacity for larger instruments as well as a higher number of instruments. To maintain sterility of items post-sterilization, hospital Sterile Processing departments are required to designate areas as "contaminated" or as "sterile." Sterilized items, wrapped or unwrapped, must be removed directly from a sterilizer after being sterilized and into a designated sterile area to prevent instrument or packaging exposure to environmental microbial contaminants. This is achieved in hospital settings and some larger clinics by utilizing large, floor-standing, double-door steam sterilizers having an entry door on the contaminated side of the Sterile Processing Department and an exit door on the sterile side of the Sterile Processing Department.

Healthcare has evolved into more specialized services and availability through local neighborhood clinics and settings. These smaller facilities have neither space to accommodate nor an instrument processing volume to justify use of a large steam sterilizer normally used in hospital Sterile Processing departments. However, with healthcare-acquired disease transmission increasing in both incidence and severity, smaller healthcare facilities require similar attention in mitigating disease transmission by ensuring sterilized items are directly placed into a sterile area after sterilization processes.

The Cox sterilizer has inherent design limitations that limit its ability to accommodate a double door configuration and to expand sterilization chamber dimensions required for increased instrument capacity and instrument size. The existing vertical orientation of airflow into the chamber precludes the use of the Cox sterilizer as a double door, pass-through sterilization device as the device requires the back of the sterilization chamber for the plenum which houses the fan wheel and the heater element. These components would require relocation to one side of the unit to accommodate a rear door opposite the front door for direct pass-through of post-sterilized instruments to a sterile area, which would further impact the efficacy of the device.

Reconfiguration of airflow from vertical orientation to horizontal orientation into the sterilization chamber would require airflow supply to traverse a distance at least double that of the Cox device. It has further been demonstrated that expansion of the vertical airflow distance beyond four inches significantly alters airflow velocity, which dramatically reduces air mixing and leads to reduced microbial kill efficacy. Such limitations would preclude a sterilization chamber with horizontal airflow from having a chamber width greater than four inches.

The design embodied by Cox et al. did not produce an airflow with temperature uniformity prior to reaching the sterilization chamber. To compensate for the wide temperature ranges created as a result of heater element orientation and short air pathway to the sterilization chamber, the Cox device relies on a waffled jet plate, an air deflector plate, and a plenum diversion insert to achieve an adequate temperature uniformity for instrument sterilization. The use of these mechanisms increased air turbulence in the sterilization chamber to narrow a temperature range of the heated air supply entering the sterilization chamber from a temperature ranging from 400 to 600 degrees Fahrenheit to a tolerable temperature ranging from 380 to 410 degrees Fahrenheit within the sterilization chamber.

In a computational fluid-air dynamics analysis of the Cox sterilizer conducted by the Rochester Institute of Technology using airflow simulation, a two hundred-degree Fahrenheit temperature variation was observed in airflow immediately after heater element exposure. Airflow mixing by the air supply jet plate and top wall diverter plate allowed adequate mixing to occur as shown in this simulation, but pockets of air remained within the sterilization chamber having temperature range variations of twenty to thirty degrees Fahrenheit or more caused by resultant eddy currents. The simulation analysis, when compared to actual thermocouple measurements demonstrated accurately the observations of temperature variation within the sterilization chamber.

BRIEF DESCRIPTION OF THE INVENTION

Embodiments of the present invention provide an apparatus and process for sterilization of items, most notably surgical instruments, used in medical, dental, veterinary, or other patient-care markets. The invention relates, more particularly to an improved high velocity dry heat sterilization device that can be utilized to allow transport of post-sterilized items through a sterilizer directly into a sterile area by way of a second door opposite the entry door of the sterilizer.

The present invention comprises a high velocity, hot air sterilization device for sterilizing medical, dental, or veterinary instruments or other objects used in critical-care environments. The sterilization device improves upon devices known in the art by: (1) incorporating a double door configuration to allow pass-through access of post-sterilized instruments directly into a sterile instrument processing area; (2) providing an air supply heating system configured to minimize high and low temperature extremes from a heating unit that typically cause uneven and uncontrollable temperature variations in an airflow pathway; (3) providing a dual airflow pathway by which recirculated and reheated air is supplied to a sterilization chamber with uniform heat distribution and horizontal airflow velocity to meet parameter requirements of high velocity hot air sterilization within the sterilization chamber; and (4) providing a temperature sensing monitor disposed within the sterilization chamber that accounts for instrument load mass variances and controls initiation of a sterilization cycle to assure required microbial inactivation thresholds are met.

In an embodiment of the invention, the sterilization device comprises: (1) a double door configured to allow efficient pass-through of sterilized instruments, objects, and instrument cassettes directly through a sterilization chamber to a sterile instrument processing area, thereby avoiding environmental conditions which may re-contaminate sterilized articles; (2) at least one control configured to regulate opening and closing of a non-sterile entry door and of a sterile exit door to prevent an open pathway between contaminated areas and sterile areas of an instrument processing facility through both doors being open at a given time; (3) a sterilization chamber configured to accommodate increased size and volume of instruments and containers required for patient care through uniform heat distribution within the chamber; (4) an air supply heating system configured to generate and deliver high velocity hot air to instruments, objects, or instrument cassettes within the sterilizer chamber; (5) an air supply system further configured deliver only high velocity and thermally uniform hot air to a sterilization chamber allowing identical sterilization parameters of time and temperature prescribed by instrument sterilization regulations; (6) at least one temperature sensor disposed within the sterilization chamber configured to monitor sterilization chamber temperature, account for instrument load weight and mass variables, and initiate pre-set sterilization cycles; and (7) a closed system wherein all sterilizer doors, air handling plenums, vents, and other potential air infiltration areas are sealed to prevent the flow of external air into the air handling system or sterilization chamber during the sterilization cycle, thereby maintaining a sterile environment within the sterilization chamber.

The present invention comprises a sterilizer device having an entry door at a front end of a sterilization chamber and an exit door at a back end of a sterilization chamber. The sterilizer is further configured to allow non-sterile, contaminated instruments and instrument containers to be inserted into the sterilizer from a contaminated area of an instrument processing facility and, once sterilized, allows removal from the sterilizer chamber into a sterile area of the instrument processing facility. The sterilization device may be further configured such that only an entry door or exit door may be open at any one time, to prevent an open pathway between the contaminated area and the sterile area. In some embodiments, both an entry side and an exit side of the sterilizer device have separate control panels with touch screen controls to monitor and control door operation, internal temperature status, and sterilization cycle status. The device may also be configured to repeat sterilization cycles until sterilization of a given instrument load is successful. The sterilizer may also be configured to allow removal only through the entry door and into the non-sterile area where an unsterilized load requires removal from the sterilizer. In some embodiments, the sterilizer may be installed through a common wall between a contaminated area and a sterile area with only a single electrical connection required for operation.

In another embodiment of the invention, the sterilizer may have an air handling system comprising a fan wheel, an electric heater unit, dual hot supply air plenums, an air supply wall, a sterilization chamber, and an air return exhaust having a connection with the sterilization chamber and the fan wheel for air recirculation through the system. The air handling system may comprise a completely sealed and closed system, configured to eliminate the infiltration of outside air once a sterilization cycle is initiated, including sealing a motor shaft connected to the fan wheel.

In another embodiment, the air handling system brings air to a necessary velocity by means of a fan wheel. Air is then discharged to an air pathway, directed by generated air pressure and velocity into both an upper supply air plenum and a lower supply air plenum. Prior to entering the upper supply air plenum and the lower supply air plenum, the air supply is directed into contact with at least one electric heating unit located proximal and downstream of the fan wheel. The at least one electric heating element may be so positioned in order to maximize airflow contact and bring the air supply to a target temperature with minimal temperature variation. The air supply is then directed by the upper supply air plenum and the lower supply air plenum into the air entry plenum, which is configured to direct the air supply into the sterilization chamber through a perforated wall on a side opposite a wall attached to an air exhaust and the fan wheel. During air transit through the plenums and prior to entry into the sterilization chamber, the high velocity air is mixed to achieve temperature uniformity. The high velocity air enters the sterilization chamber, moving horizontally lateral across the sterilization chamber, toward and through an air exhaust portal and back into the fan wheel for recirculation.

In some embodiments of the invention, the sterilizer may comprise a mechanism for heating recirculated air to a required temperature with minimum temperature variation through a combination of a modulated heating unit system, heating unit position in an air pathway, and feedback sensor control.

In some embodiments of the invention, the sterilizer may be configured to deliver an air supply of uniform temperature and high velocity to a sterilization chamber having multiple dimensions with lateral or vertical airflow. The sterilizer may be further configured to continuously recirculate air to maintain a required air velocity and temperature for a duration of a given sterilization process.

In some embodiments of the invention, the air handling system of the sterilizer may be configured as sealed, closed, and configured to retain positive pressure relative to an outside environment in order to prevent infiltration of external, non-sterile air into the sterilizer air handling system during a sterilization cycle.

In another embodiment of the invention, the sterilizer may comprise at least one temperature sensor and at least one timer integrated with a controller configured to monitor, maintain, control, and record desired temperatures and sterilization cycle times to ensure proper sterilization conditions. The monitoring devices may further be integrated with a controller. In some embodiments, the heater unit and at least one temperature sensor may be integrated with a proportional-integral-derivative controller and configured to receive, monitor, and compare temperature input data with a preset required temperature. In another embodiment, the controller may comprise a microcontroller-based system having high-resolution analog-to-digital converters (ADC) configured to read a monitoring device input data such as temperature and further provide control of an output device such as a blower, heater, alarm, door locking mechanism, or sterilization chamber access restrictions. The controller may further be integrated with an input system, such as a suitable interface, configured to allow a user to review, monitor, and change system settings and status, and to otherwise control the sterilizer.

In another embodiment of the invention, the sterilizer further comprises an insulation cavity surrounding the sterilization chamber configured to provide temperature insulation and to retain heat in the sterilization chamber and within the supply air plenums.

In another embodiment, the sterilizer comprises a locking mechanism disposed within at least one door and configured to maintain an airtight seal during a sterilization process and to prevent access to the sterilizer chamber prior to completion of a sterilization cycle.

In another embodiment, the sterilizer may be configured to accept multiple layers of instruments, instruments that are uncovered, instruments on perforated trays, or instruments in baskets. It may also be configured to accept instruments and cassettes that are wrapped or pouched.

The methods, systems, and apparatuses are set forth in part in the description which follows, and in part will be obvious from the description, or can be learned by practice of the methods, apparatuses, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed. More details concerning these embodiments, and others, are further described in the following figures and detailed description set forth herein below.

DETAILED DESCRIPTION

The present invention is described in reference to the accompanying drawings and following embodiments that are presented for the purpose of illustration and should not be construed to limit the scope of the invention thereto.

The present invention relates to medical instrument sterilization. Particularly, a high velocity hot air sterilization apparatus suitable for loading instruments and their containers into the sterilization chamber by means of an entry door and subsequent to the sterilization process removing said instruments and containers by means of a separate exit door into a sterile area of the facility to mitigate environmental contaminant exposure to the sterilized instruments and containers. The sterilization apparatus comprises a housing having an entry door at a front end of a sterilization chamber and an exit door at a back end of the sterilization chamber; the chamber configured to allow non-sterile, contaminated instruments and instrument containers to be inserted into the sterilization chamber from a contaminated area of an instrument processing facility and, once sterilized, allows removal directly from the sterilization chamber into a sterile area of the instrument processing facility.

Figure 1:
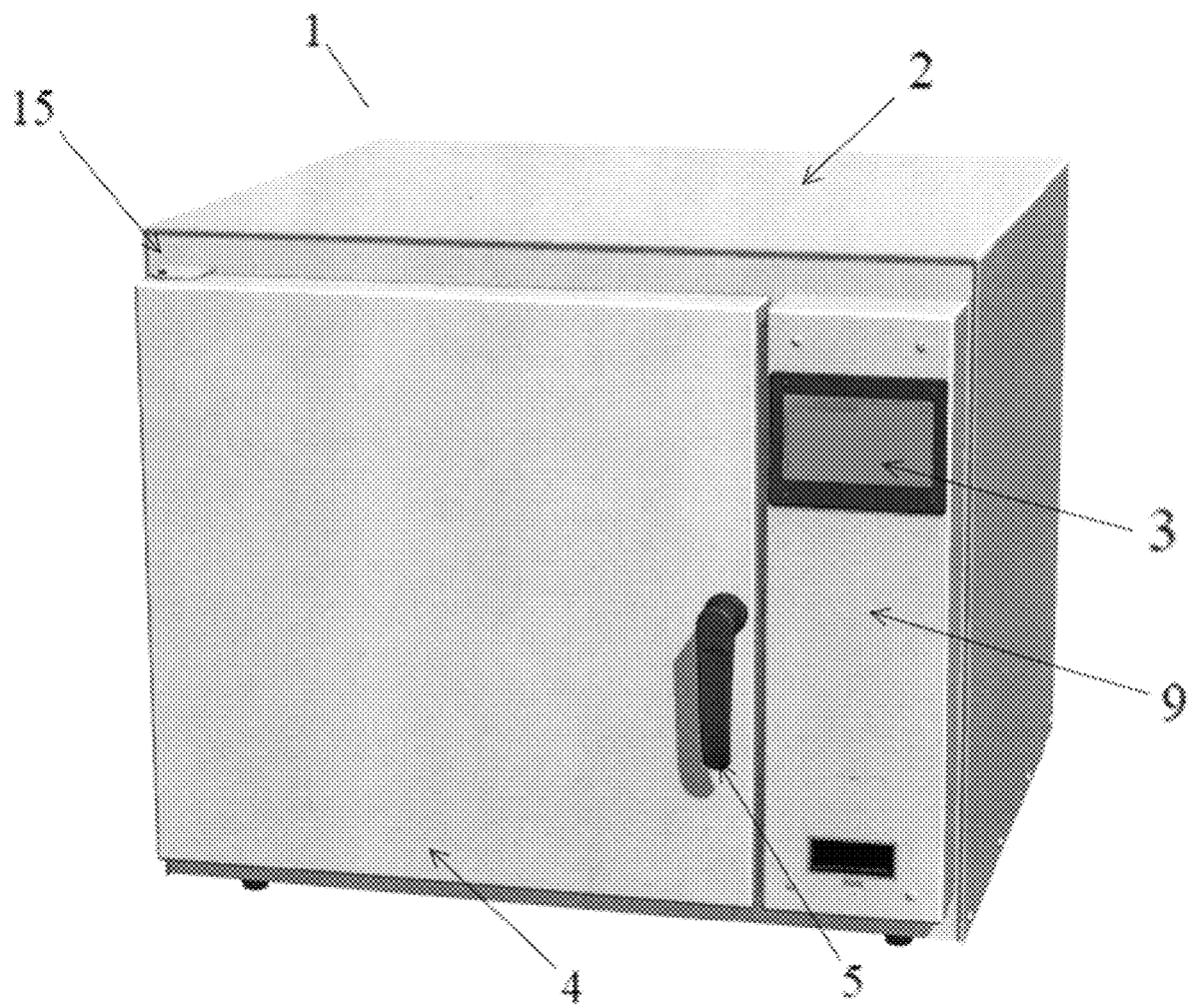
FIG. 1 illustrates a perspective view of the dual-pass through high velocity hot air sterilizer of the invention.
Figure 2A:
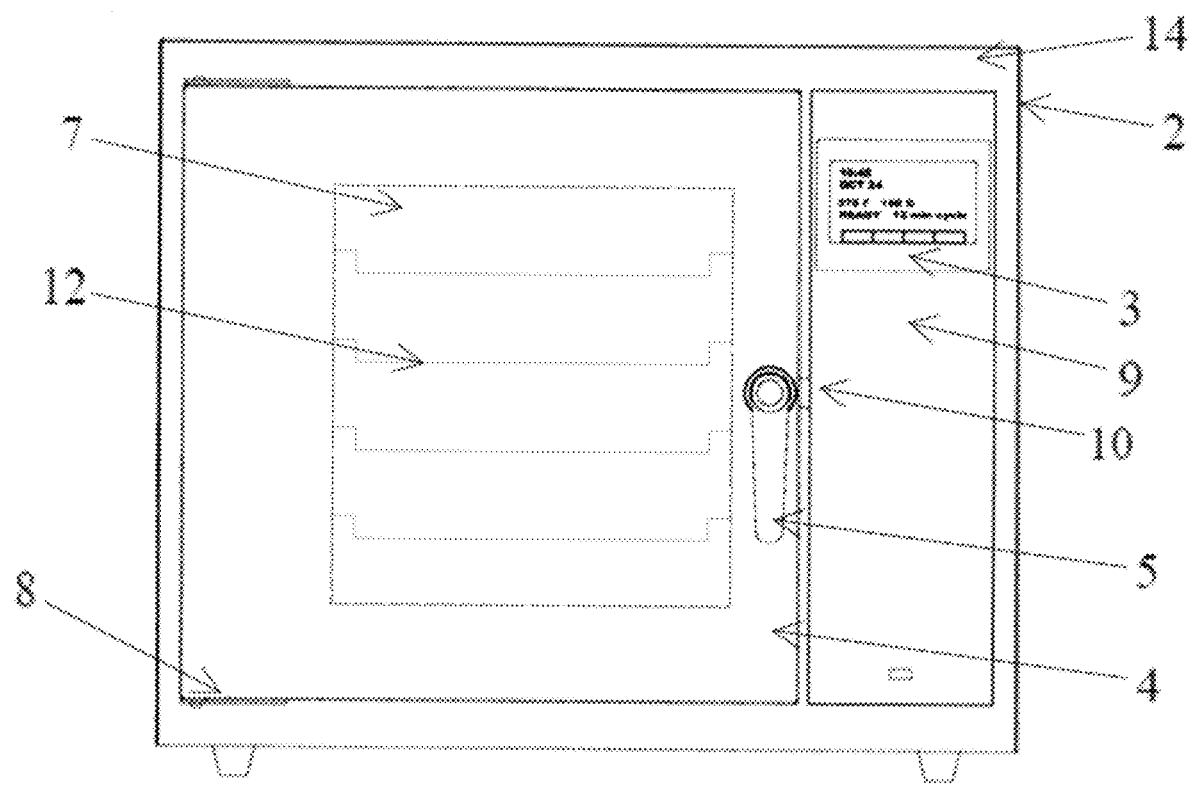
FIG. 2A illustrates profile view of the front of the sterilizer indicating the relative location of sterilization chamber.
Figure 2B:
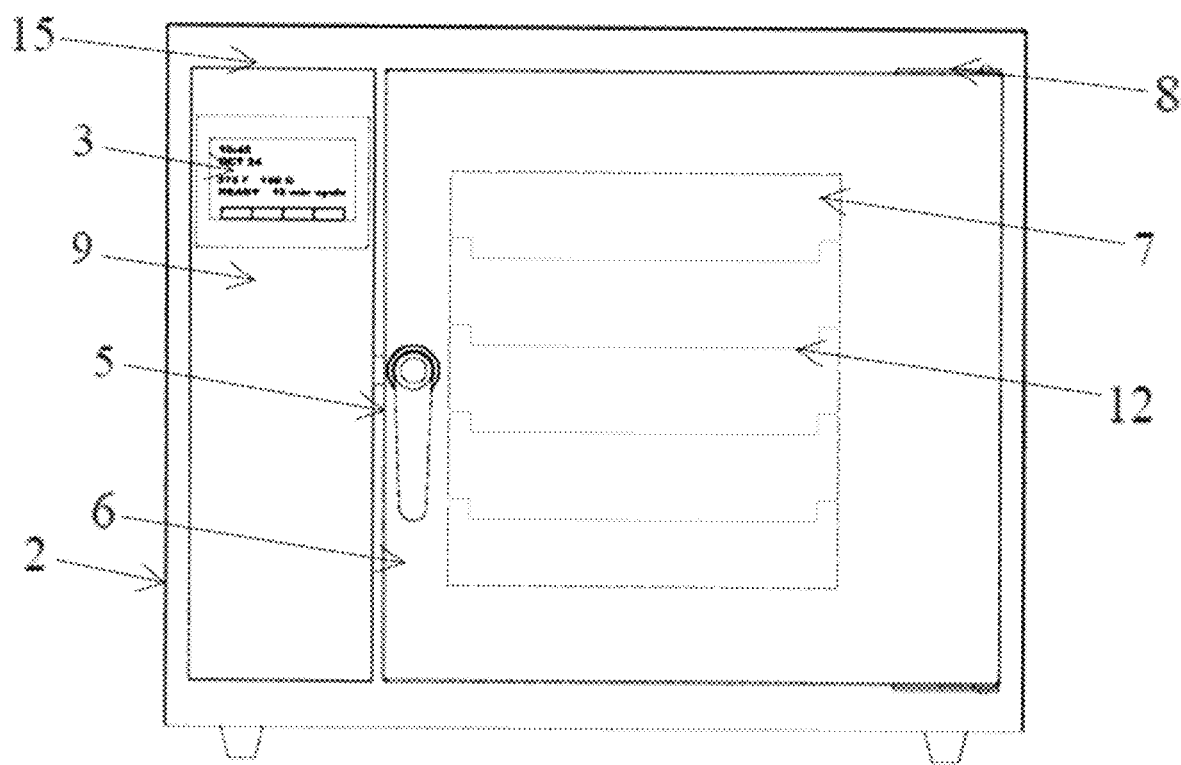
FIG. 2B illustrates a profile view of the rear of the sterilizer indicating the relative location of the sterilization chamber.
Figure 3:
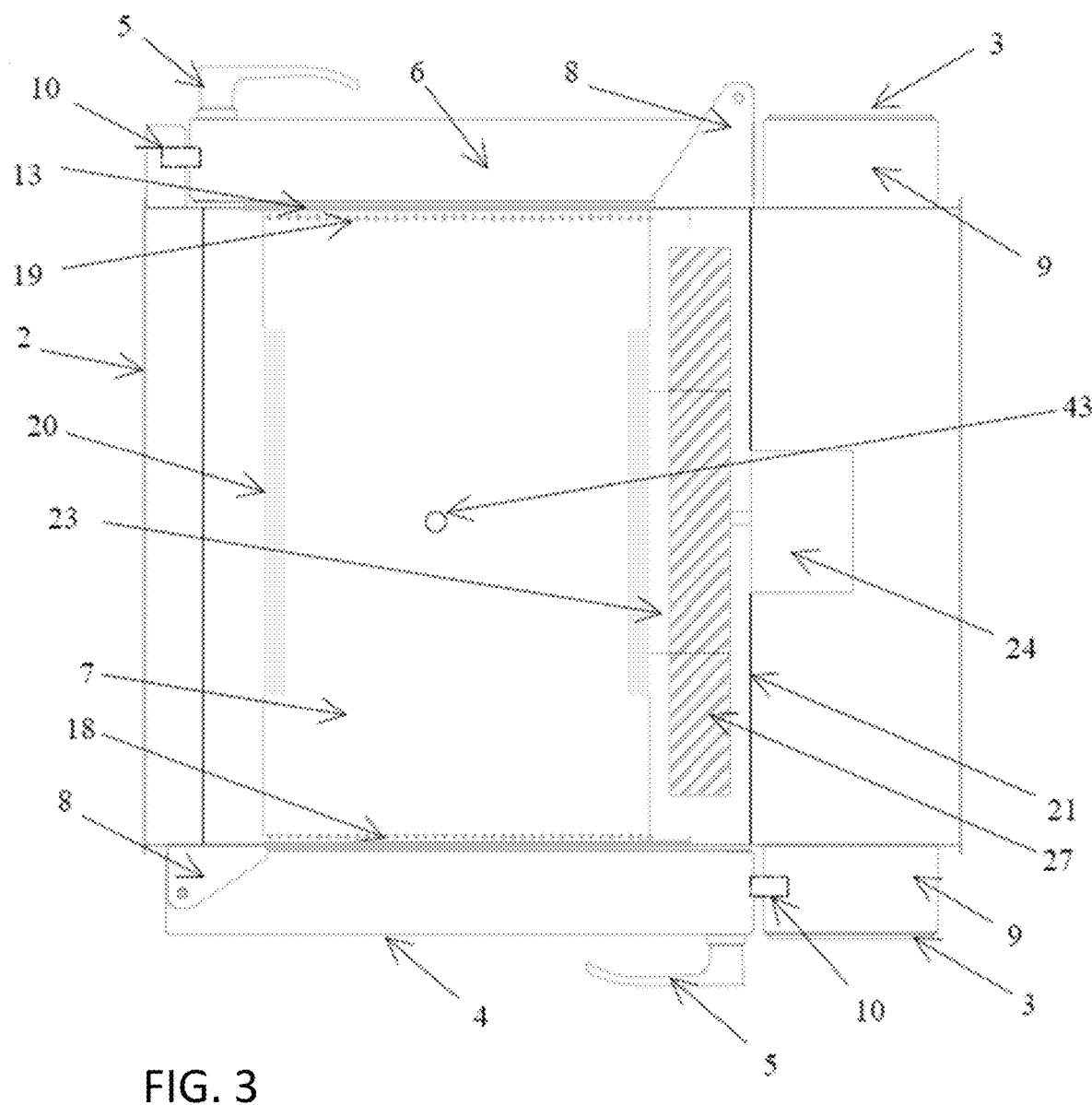
FIG. 3 illustrates a cross-sectional top view of sterilizer with both doors in a closed position, indicating the locations of the sterilization chamber and the heating chamber.
Figure 4:
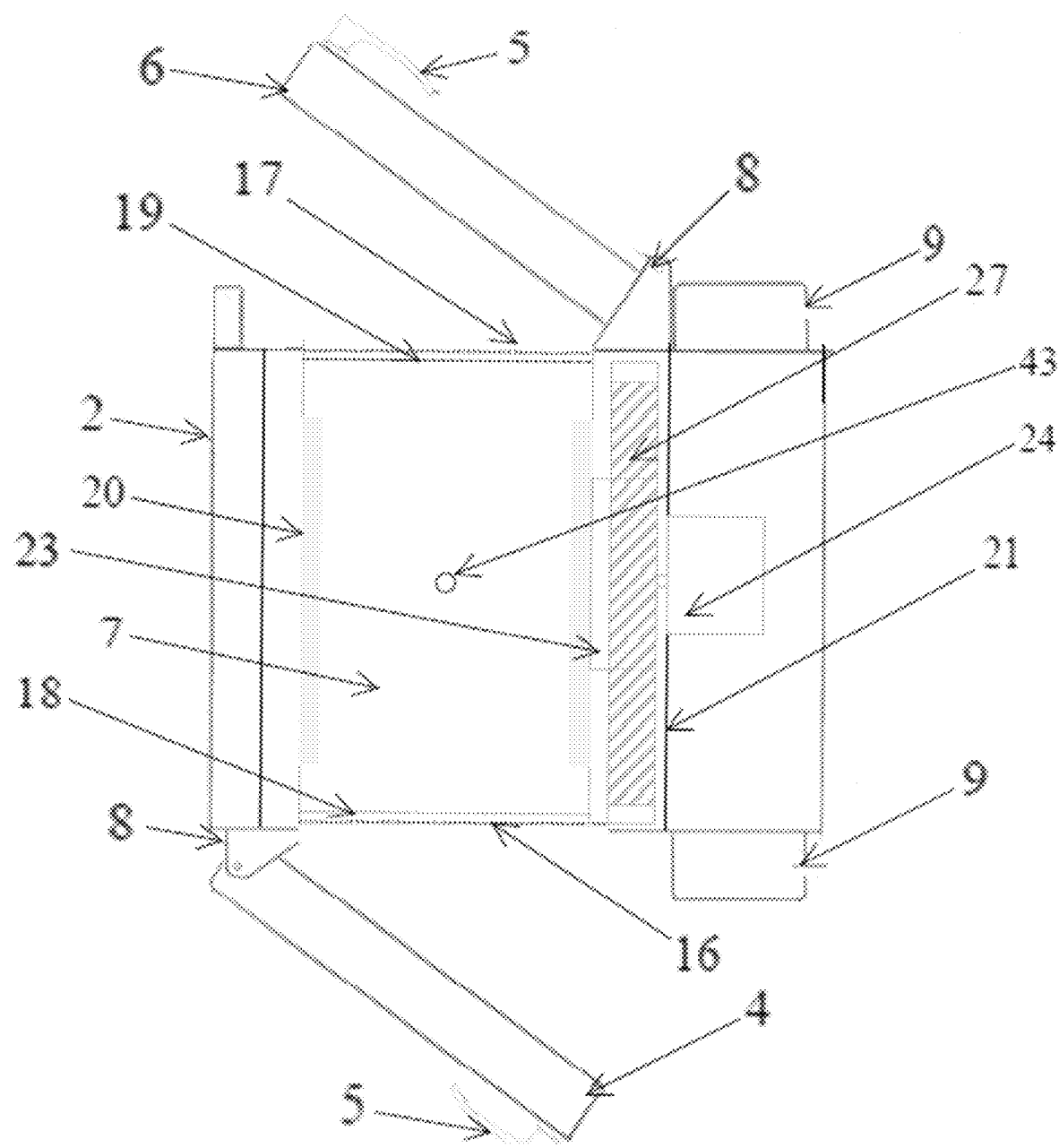
FIG. 4 illustrates a cross-sectional top view of sterilizer both doors in an open position, indicating the location of the sterilization chamber.

Referring to FIGS. 1-3, a sterilizer, alternatively referenced herein as a high velocity hot air sterilization apparatus 1, is provided which is suitable for the loading of contaminated, non-sterile instruments and their containers through an entry door 4 located at the front of the apparatus and the post-sterilization removal of said instruments and containers through an exit door 6 located at the rear of the apparatus 1. The sterilization apparatus 1 includes an outer housing 2 which surrounds a heating chamber 11 on a top, a bottom, a left side, and a right side thereof. A sterilization chamber 7 is enclosed within the heating chamber 11 and is accessed through a front panel 14 and a rear panel 15 of the apparatus 1 through a front opening 18 and a rear opening 19 of the sterilization chamber 7.

Referring to FIGS. 2A, 2B, 3, and 4, the sterilization chamber 7 is accessed for instrument insertion via a front entry door 4 and through an opening 16 disposed through the front panel 14 of the apparatus and through the front opening 18 of the sterilization chamber 7. Instruments and containers may be placed on perforated instrument trays 12 which are coupled within the sterilization chamber 7 by parallel tray rails 20. Similarly, sterilized instruments may be removed from the sterilization chamber 7 through the rear opening 19 of the sterilization chamber 7, through the rectangular opening 17 disposed through the rear panel 15. The entry door 5 and the exit door 6 are attached to the front panel 14 and the rear panel 15, respectively, by a plurality of pivot hinges 8 configured to allow the entry door 5 and the exit door 6 to move between an open position and a closed position. The entry door 4 and exit door 6 be hinged vertically or horizontally.

During a sterilization cycle, the entry door 4 and the exit door 6 are each configured in a closed position and are each locked into place by a turning locking door handle 5, disposed upon each door and which activate a door lock 10, thereby sealing door gaskets 13 tightly against the entry door 4 and the exit door 6 during the sterilization cycle to prevent outside air from entering the heating chamber 7. The sterilization apparatus 1 may be configured such that only the entry door 4 or the exit door 6 may be in an open position at a given time, thereby preventing an open pathway between a contaminated area and a sterile area of the sterile processing area. This function may be controlled and monitored by through a touch pad controller 3 by means of an electrical control panel 9.

Figure 5:
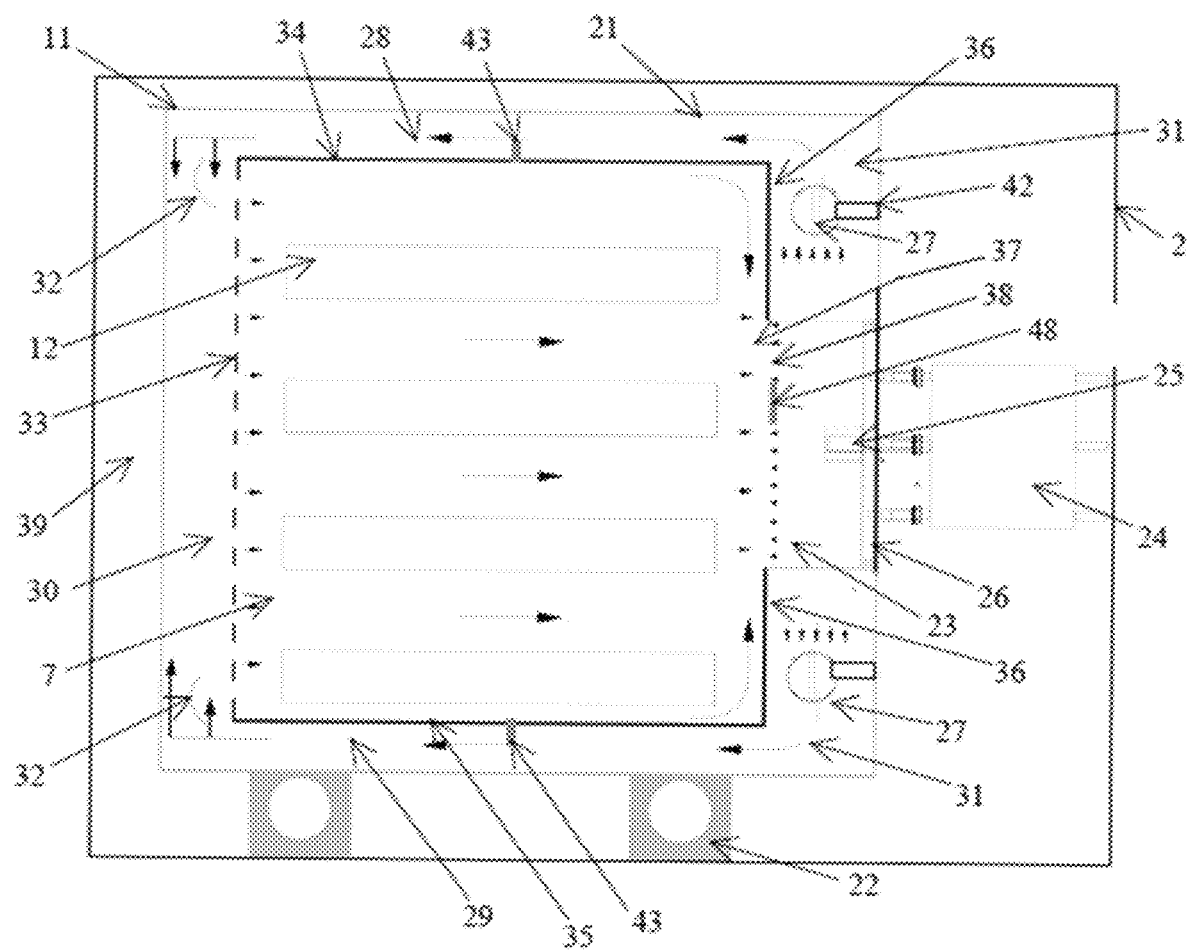
FIG. 5 illustrates a cross-sectional view of the sterilizer depicting the air handling system and airflow direction.
Figure 6:
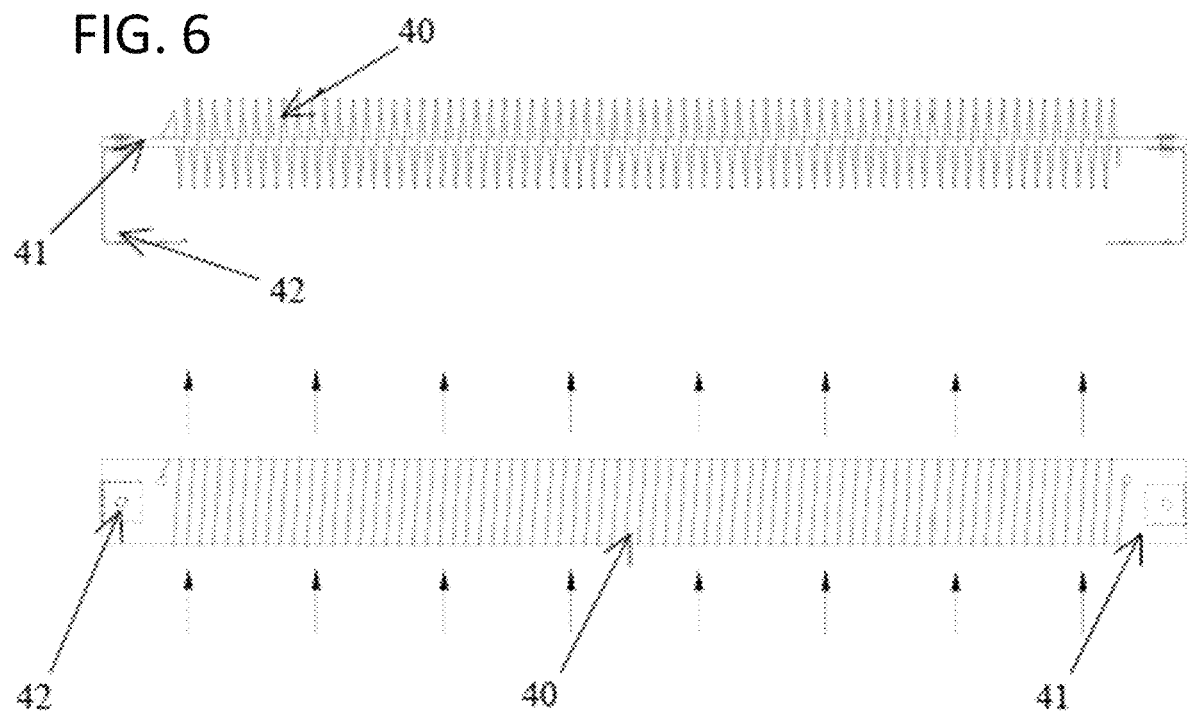
FIG. 6 illustrates a profile view of a heating element of the invention and a resulting lateral airflow.
Figure 7:
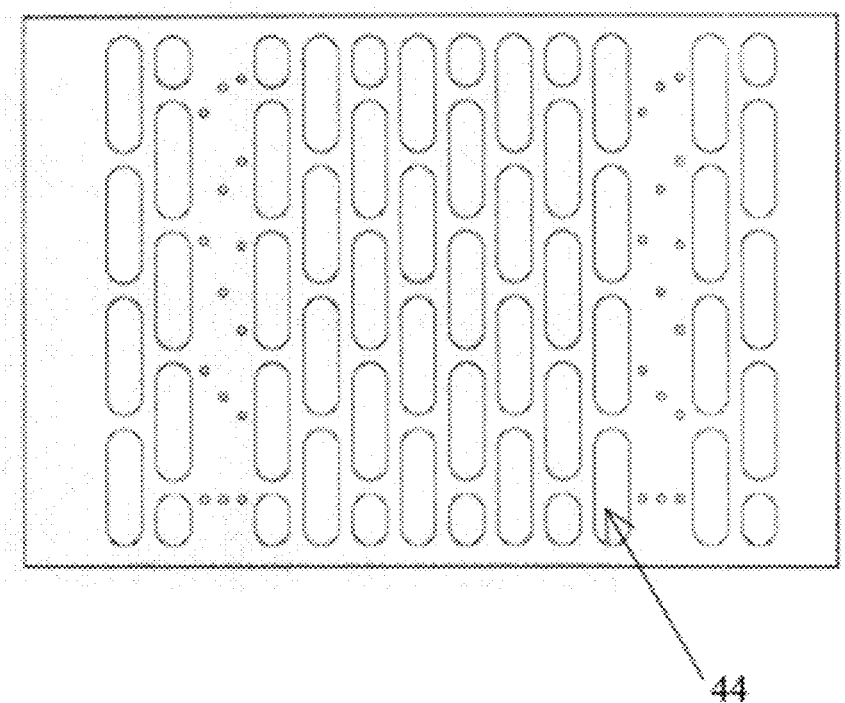
FIG. 7 illustrates a profile view of a perforated air supply wall of the invention.

Referring to FIGS. 3 and 5, a heating chamber 11 is defined by a plurality of heating chamber walls 21 which form a plurality of sides, a top, and a bottom of the heating chamber 11; the chamber walls configured to preclude entry of outside air into the heating chamber 11, thereby allowing the heating chamber 11 and an associated air handling system to remain airtight and isolated when the entry door 4 and the exit door 6 are in a closed position and locked during a sterilization cycle. Encompassing an exterior of the heating chamber 11, an insulating cavity 39 is disposed between an interior face of the outer housing 2 and an exterior face of the heating chamber wall 21. The heating chamber 11 is coupled to and supported within the outer housing 2 of the sterilization apparatus 1 by a plurality of support brackets 22 and attachment to the outer housing 2 and front panel 14 and rear panel 15 of the sterilizer 1 to create the insulation cavity 39 containing an insular material such as fiberglass. The insulation cavity 39 serves two purposes. The first purpose is to minimize heat loss from the heating chamber 11 during the sterilization cycle. The second purpose is to provide a heat barrier between the heating chamber 11 and the metal outer housing 2 of the high velocity hot air sterilizer 1.

Referring to FIG. 5, the sterilization apparatus 1 includes an air handling system comprising a circulation fan 23, an upper heating element 27, a lower heating element 27, dual air handling pathways, and sterilization chamber 7. The air handling system directs supply air originating at the circulation fan 23. An air handling pathway traverses each above and below the sterilization chamber 7 by means of an upper supply air plenum 28 and a lower supply air plenum 29 formed by an external face of each a top wall 34 and a bottom wall 35, respectively, of the sterilization chamber 7 and an internal face of the heating chamber wall 21. An air entry plenum 30 is formed by an internal face of the heating chamber wall 21 and an external face of a perforated supply air wall 33 disposed through the sterilization chamber 7. An air exhaust plenum 31 houses the circulation fan 23 and upper and lower heating elements 27. The air exhaust plenum 31 is formed by an interior face of the heating chamber wall 21 and an exterior wall of the sterilization chamber 7, the exterior wall having an exhaust disposed therethrough to form an exhaust wall 36. The exhaust wall 36 comprises an exhaust portal 37 configured to allow access to the circulation fan 23. The exhaust portal 37 may be covered by a mesh screen 38. A motor 24, located externally to the heating chamber 11, is connected to the circulation fan 23 by a motor shaft 25 configured to drive the circulation fan 23 through electromechanical force. A seal 26 is further disposed around the motor shaft 25 and upon an interior face of a heating chamber wall 21, the seal 26 configured to prevent air infiltration into the heating chamber 11 by way of the motor shaft 25.

Referring to FIGS. 4, 5, 6, and 7, the circulation fan 23 creates positive pressure and air velocity, which in turn drives air through an upper vertical portion and a lower vertical portion of the air exhaust plenum 31. Immediately above and below the circulation fan 23, the heating elements 27 are positioned and configured to maximize contact between the heating elements 27 and air emitted from the circulation fan 23. The heating elements 27 may comprise a metal heating coil 40 wound around an electrical insulator 41 and may be attached to an interior face of the heating chamber wall 21 by a mounting support 42 coupled at each end of each heating element 27. Air is then directed laterally over the heating elements 27 to thereby maximize air exposure to each heating element 27. The air, now heated, then enters a horizontal upper supply air plenum 28 and a horizontal lower supply air plenum 29 each plenum having a ninety-degree turn and a temperature sensor 43, such as a thermocouple, disposed upon a surface of both the horizontal upper supply air plenum 28 and the horizontal lower supply air plenum 29. The temperature sensor 43 is coupled to and in connection with an electronic controller configured to relay temperature data and allows control of activation or inactivation of the heating elements 27 to thereby minimize air temperature deviations after exposure to the heating elements 27. The air then moves through the upper supply air plenum 28 and the lower supply air plenum 29 and enters the air entry plenum 30, the air entry plenum 30 having a ninety-degree turn formed in its path.

Air then enters the sterilization chamber 7 through a plurality of perforations 44 in the perforated supply air wall 33 of the sterilization chamber 7. To assist in uniform distribution of airflow within the sterilization chamber 7, a plurality of airflow diverters 32 may be disposed at junctions of the upper supply air plenum 28 and lower supply air plenum 29 of the air entry plenum 30 in order to evenly direct air across the perforated supply air wall 33. Dependent on a need for additional airflow distribution to the sterilization chamber 7, other airflow diverters 32 may also be disposed in other locations throughout the airflow pathway. The air supply, now uniform in temperature, then enters the sterilization chamber 7 through the perforated supply air wall 33, traversing horizontally across a width of the sterilization chamber 7 and toward the air exhaust wall 36 as directed by a negative pressure created by the circulation fan 23. Air is then pulled from the sterilization chamber 7 through the air exhaust portal 37 and enters the circulation fan 23. A screen 38 is coupled to and spans the air exhaust portal 37, configured to protect the circulation fan 23 from loose objects that may enter from the sterilization chamber 7.

Referring to FIG. 5 a cycle control temperature sensor 48 may be disposed within the sterilization chamber 7 near a center of the exhaust port screen 38, the temperature sensor configured to account for variances in instrument masses that may exceed a prescribed parameter limit and influence time required for instrument sterilization. The cycle control temperature sensor 48 is further configured to monitor the sterilization chamber 7 and exit temperature of the air flowing over instruments within the sterilization chamber as the air enters the sterilization air exhaust port 37 for re-heating and recirculation.

During instrument heating, heated air flowing over colder instruments will be cooled from an air supply portal 44 having an entry temperature of 375 degrees Fahrenheit. This temperature is monitored by the cycle control temperature sensor 48 and as instrument temperatures increase, a rate of chamber air temperature increase will slow, approaching 375 degrees Fahrenheit as the temperature sensor modulates the system. At this point, instruments within the sterilization chamber will have reached a threshold temperature necessary to initiate bacterial spore kill. Further, at this point a temperature sensor measurement may be used to initiate a sterilization cycle timing necessary to achieve a 12-Log kill of bacterial spores.

Figure 8:
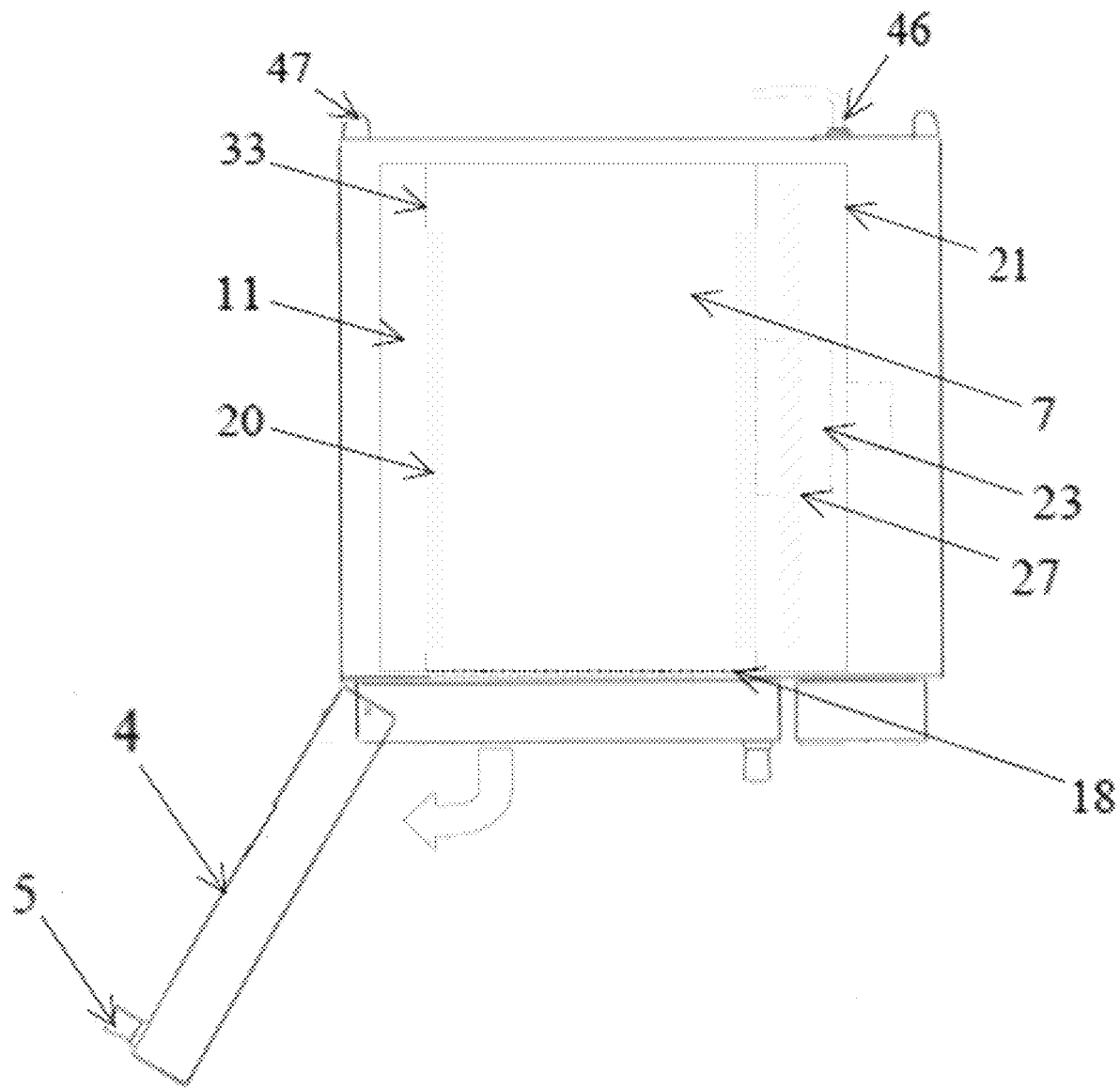
FIG. 8 illustrates a top profile view of another embodiment of the sterilizer indicating the location of the heating chamber.

Referring to FIG. 8, the sterilization apparatus 1 may be configured for use with instruments inserted and removed in a single area. In this embodiment the apparatus 1 has a single entry door 4 for inserting non-sterile instruments into the apparatus 1 and a sterilization chamber 7 having only a front opening 18 and enclosed by a top, a bottom, a back, and a plurality of sides. Upon completion of a sterilization cycle, the entry door 4 is unlocked and opened for sterilized instrument removal. In such an embodiment, the sterilization chamber 7 is enclosed within a heating chamber 11 defined by a heating chamber wall 21, the chamber wall having recirculating fan 23 disposed thereon, an upper heating element 27 and a lower heating element 27, and dual air pathways identical to all aspects of the air handling system in the double door configuration of the sterilizer 1, as discussed above. Spacers 47 may be disposed upon an exterior surface of a rear wall of the sterilization apparatus 1 and configured to facilitate air circulation between the wall and the apparatus 1.

In some embodiments of the invention, the sterilization apparatus, sterilization chamber, and all other components may comprise materials capable of withstanding temperatures utilized in high velocity hot air sterilization, such as 375 degrees Fahrenheit or higher. The materials may include, but are not limited to, stainless steel, aluminum, high temperature resistant thermoplastic and thermosetting polymers, ceramics, silicone, or nylon plastics.

In some embodiments, the heater unit and at least one temperature sensor may be integrated with a proportional-integral-derivative controller and configured to receive temperature sensor input and compare recorded air temperature with a required control temperature and relay data to activate or inactivate a heating unit. The controller may further comprise a microcontroller-based system having high-resolution analog-to-digital converters (ADC) configured to read a monitoring device input data such as temperature and provide control of an output device such as a blower, heater, alarm, door locking mechanism, or sterilization chamber access restrictions. The controller may further be integrated with an input system, such as a touch screen, keyboard, or other suitable interface, configured to allow a user to change prescribed settings, initiate or end a sterilization cycle, and generally control the apparatus, including and locking and unlocking coordination of the door or doors of the apparatus 1. Further, the controller may also comprise operating instructions and system status information for review and monitoring by a user through a display system such as an LCD or LED display.

The sterilization apparatus may be further configured such that only one entry door or exit door may be open at a given time, thereby preventing an open pathway between a contaminated area and a sterile area of the instrument processing facility. In some embodiments, both an entry side and an exit side of the sterilization apparatus may have separate control panels with user interface controls to assure to an operator that sterilization conditions have been achieved and that the entry door is closed and locked before the exit door can be unlocked and opened to the sterile area following a successful sterilization cycle. If required conditions are not met for a given sterilization cycle, the sterilization cycle may be repeated until successful. If an unsterilized load requires removal from the apparatus, the apparatus may be configured such that removal may only be done through the entry door and into a non-sterile area of the instrument processing facility. In some embodiments, the apparatus may comprise a specialized outer housing configured to allow installation of the apparatus through a common wall between a contaminated area and a sterile area with only a single electrical connection required for operation thereof.

To meet the airflow dynamics required in obtaining uniform heat distribution and airflow velocity that allow for parameters necessary in high velocity hot air sterilization requires an air handling design that ensures the delivery of an air supply having a minimized temperature variation range before entering the sterilization chamber, alleviating the need for a jet plate and an air deflector or other devices to generate air turbulence for mixing air to temperature uniformity. Such an air supply system allows varying sterilizer chamber dimensions, relying solely on the air supply to be delivered both uniformly across the air supply wall and into the sterilization chamber to assure conditions for high velocity hot air sterilization whether having a vertical or horizontal airflow.

Two critical factors influence temperature uniformity in supply air before entering the sterilization chamber: design and length of an air pathway and configuration, placement, and control of the heating element at the beginning of the air pathway. Although the length and design of the air pathway is important in allowing time, distance and airflow interference to homogenize air temperature, this factor alone will not assure temperature uniformity at air entry point to the sterilization chamber. Increased pathway length, plenum diversions, and ninety-degree turns will assist in air mixing, but large variations in air temperatures generated by heating element exposure cannot be offset by these design components.

Minimizing temperature variations within the supply air pathway can be achieved with the proper design, placement, and control of a heating element. The importance of the heating element as a critical factor for air temperature variation control has not been implemented in the art; with most devices relying on pathway modifications to compensate for temperature extremes created by heating a recirculated air supply. Orientation of a heating element to the airflow is critically important, as well as maximizing the amount of air exposed to the heating element in order to minimize air temperature extremes produced as a result of heated and unheated or minimally heated air. Employing a heating element of low thermal mass enables more rapid response from a temperature sensor and its controller by minimizing temperature overshoot and undershoot, generating heated air with less temperature extremes. Temperature sensor placement is critical in obtaining downstream air temperature data necessary in modulating the heating element for constant temperature maintenance and further minimizes temperature extremes. Placement of temperature sensors downstream within the supply air plenum in contrast to the sterilization chamber allows for better representation of air temperature homogenization and enables faster responses to a temperature controller. The controller receives the temperature sensor input and compares the actual temperature with the required control temperature and relays the data to activate or deactivate the heating element. The use of a proportional-integral-derivative controller further optimizes sterilization chamber warm-up, more precisely maintain plenum temperatures, minimize temperature overshoot and undershoot, and speed heating element response.

A third temperature sensor located within the sterilization chamber at the air exhaust port further serves to monitor sterilization chamber temperatures during the sterilization warm-up, instrument heating, and sterilization cycle. Air pre-heated to 375° F. travels horizontally through the sterilization chamber and across the instruments before entering the exhaust portal for re-heating and recirculation. Heated air passing across the instruments is cooled as the heat from the air is transmitted to the instruments. As the sterilization process proceeds during instrument heating, the temperature measured at the exhaust portal increases as the temperature differential between the instruments and heated flowing air decreases. Initiation of microbial inactivation begins once the sterilization threshold temperature is reached on the instruments. The time required to reach the sterilization temperature threshold varies according to the mass of the instrument load. The temperature sensor located at the exhaust portal provides a quantitative measure indicating when the instruments in the sterilization chamber have achieved this minimum sterilization threshold temperature. Once the critical exhaust portal temperature has been achieved that data is relayed to activate the sterilization cycle. Since instrument mass may vary from load to load, this quantitative measure is critical to assuring that required instrument temperature thresholds are achieved and maintained for a pre-requisite time to assure the level of microbial inactivation required.

There are no existing sterilizers in the art that feature a double door configuration that can provide entry of contaminated instruments into a sterilizer from a contaminated area and subsequently, post-sterilization, have direct pass-through access into a sterile area through a second, exit door from that same sterilizer. A need exists for a high velocity hot air sterilization device capable of accommodating higher throughput capacities and larger instruments, having a double door design that allows direct pass-through of post-sterilized instruments to a sterile environment, all while still maintaining thermal uniformity and microbial kill efficacies within the sterilizer chamber.

The present invention attempts to remedy the shortcomings of prior art sterilizers by providing a high velocity hot air sterilization apparatus capable of accommodating higher capacities and larger instruments through a double door design that allows direct pass-through of post-sterilized instruments to a sterile environment while still maintaining thermal uniformity and microbial kill efficacies within the sterilizer chamber.

Those of ordinary skill in the art will understand and appreciate that the foregoing description of the invention has been made with reference to certain exemplary embodiments of the invention, which describe a high velocity hot air sterilization apparatus. Those of skill in the art will understand that obvious variations in system configuration, protocols, parameters or properties may be made without departing from the scope of the invention which is intended to be limited only by the claims appended hereto.

What is claimed is:

1. An air handling system comprising:
   a sterilization chamber having an air exhaust portal disposed through a side;
   an air handling pathway traversing above the sterilization chamber through an upper supply air plenum and traversing below the sterilization chamber through a lower supply air plenum;
   a circulation fan;
   an upper heating element above the circulation fan within the upper supply air plenum;
   a lower heating element below the circulation fan within the lower supply air plenum;
   a first temperature sensor disposed within the upper supply air plenum and configured to measure temperature of air downstream from the upper heating element;
   a second temperature sensor disposed within the lower supply air plenum and configured to measure temperature of air downstream from the lower heating element; and
   a third temperature sensor disposed within the sterilization chamber at the air exhaust portal and configured to monitor temperature of air exiting the sterilization chamber;
   wherein the circulation fan is configured to direct supply air from the air exhaust portal over the upper heating element through the upper supply air plenum and over the lower heating element through the lower supply air plenum; and
   wherein each of the first, second, and third temperature sensors are configured to relay respective temperature measurements to an electronic controller of a sterilizer, the electronic controller being configured to activate and deactivate the upper heating element to minimize air temperature deviations at the upper heating element, configured to activate and deactivate the lower heating element to minimize air temperature deviations at the lower heating element, and configured to initiate a sterilization cycle after the third temperature sensor measures temperature of air exiting the sterilization chamber reaching a sterilization threshold temperature.

2. The air handling system of claim 1, wherein the sterilization chamber has an air supply portal disposed through another side, and the circulation fan is configured to direct supply air through the upper supply air plenum and through the lower supply air plenum into the air supply portal.

3. The air handling system of claim 2, wherein supply air is directed through a ninety-degree turn of the upper supply air plenum, and supply air is directed through a ninety-degree turn of the lower supply air plenum.

4. The air handling system of claim 2, wherein supply air directed into the air supply portal traverses horizontally across a width of the sterilization chamber toward the air exhaust portal.

5. The air handling system of claim 4, wherein supply air is cooled while traversing horizontally across the width of the sterilization chamber.

6. The air handling system of claim 1, wherein the electronic controller is configured to activate and deactivate the upper heating element by an analog-to-digital converter, and is configured to activate and deactivate the lower heating element by the analog-to-digital converter.

7. The air handling system of claim 1, wherein the upper supply air plenum further comprises a first airflow diverter at a first junction, and the lower supply air plenum further comprises a second airflow diverter at a second junction.

8. A sterilizer, comprising:
an air handling system; and
an electronic controller;
wherein the air handling system further comprises:
a sterilization chamber having an air exhaust portal disposed through a side;
an air handling pathway traversing above the sterilization chamber through an upper supply air plenum and traversing below the sterilization chamber through a lower supply air plenum;
a circulation fan;
an upper heating element above the circulation fan within the upper supply air plenum;
a lower heating element below the circulation fan within the lower supply air plenum;
a first temperature sensor disposed within the upper supply air plenum and configured to measure temperature of air downstream from the upper heating element;
a second temperature sensor disposed within the lower supply air plenum and configured to measure temperature of air downstream from the lower heating element; and a third temperature sensor disposed within the sterilization chamber at the air exhaust portal and configured to monitor temperature of air exiting the sterilization chamber;
wherein the circulation fan is configured to direct supply air from the air exhaust portal over the upper heating element through the upper supply air plenum and over the lower heating element through the lower supply air plenum;
wherein each of the first, second, and third temperature sensors are configured to relay respective temperature measurements to the electronic controller; and
wherein the electronic controller is configured to activate and deactivate the upper heating element to minimize air temperature deviations at the upper heating element, configured to activate and deactivate the lower heating element to minimize air temperature deviations at the lower heating element, and configured to initiate a sterilization cycle after the third temperature sensor measures temperature of air exiting the sterilization chamber reaching a sterilization threshold temperature.

9. The sterilizer of claim 8, wherein the sterilization chamber has an air supply portal disposed through another side, and the circulation fan is configured to direct supply air through the upper supply air plenum and through the lower supply air plenum into the air supply portal.

10. The sterilizer of claim 9, wherein supply air is directed through a ninety-degree turn of the upper supply air plenum, and supply air is directed through a ninety-degree turn of the lower supply air plenum.

11. The sterilizer of claim 9, wherein supply air directed into the air supply portal traverses horizontally across a width of the sterilization chamber toward the air exhaust portal.

12. The sterilizer of claim 8, wherein the electronic controller is configured to activate and deactivate the upper heating element and is configured to activate and deactivate the lower heating element by an analog-to-digital converter.

13. The sterilizer of claim 8, wherein the upper supply air plenum further comprises a first airflow diverter at a first junction, and the lower supply air plenum further comprises a second airflow diverter at a second junction.

* * * * *